United States Patent [19]

Erlanger et al.

[11] Patent Number: 5,756,301
[45] Date of Patent: May 26, 1998

[54] ENDOGENOUS TAXOL-LIKE SUBSTANCE IN HUMAN SERUM, MONOCLONAL ANTIBODIES DIRECTED THERETO AND METHODS OF ASSAYING THEREFOR

[75] Inventors: Bernard F. Erlanger, Whitestone; Jyh-Gang Leu; Bi-Xing Chen, both of New York, all of N.Y.

[73] Assignee: The Trustees of Columbia University in the City of New York, New York, N.Y.

[21] Appl. No.: 25,557

[22] Filed: Mar. 3, 1993

[51] Int. Cl.$^6$ ............................................. G01N 33/567
[52] U.S. Cl. .................. 435/7.23; 435/7.92; 435/240.27; 435/70.21; 435/188; 435/7.21; 436/548; 530/387.1; 530/388.1; 530/391.1; 530/391.3
[58] Field of Search .................. 435/7.92, 7.21, 435/240.27, 70.21, 188, 7.23; 436/548; 530/387.1, 388.1, 391.1, 391.3

[56] References Cited

PUBLICATIONS

Wani, M.C., et al. "Plant Antitumor Agents. VI. The Isolation and Structure of Taxol, a Novel Antileukemic and Antitumor Agent From Taxus Brevifoli" *J. Am. Chem. Soc.*, 93:2325–2327 (Nov. 1971).

Schiff, P.B., et al. "Promotion of Microtubule Assembly In Vitro by Taxol" *Nature* (Lond.), 227:665–677 (Feb. 1979).

Kumar, N. "Taxol–Induced Polymerization of Purified Tubulin" *J. Biol. Chem.*, 256:10435–10441 (Oct. 1981).

Parness, J., et al. "Taxol Binds to Polymerized Tubulin In Vitro" *J. Cell. Biol.*, 91:479–487 (Nov. 1981).

Rowinsky, E.K., et al. "The Clinical Pharmacology and use of Antitumor Agents in Cancer Chemotherapeutics" *Pharmac. Ther.*, 52:35–84 (1991).

Kingston, D.G.I. "The Chemistry of Taxol" *Pharmac. Ther.*, 52:1–34 (1991).

Longnecker, S.M., et al. "High–Performance Liquid Chromatographic Assay For Taxol in Human Plasma and Urine and Pharmacokinectics in a Phase I Trial" *Cancer Treat. Rep.*, 71:53–59 (Jan. 1987).

Leu, J.–G., et al. "Immunoassay of taxol and taxol–like compounds in plant extracts." *Life Sciences* 53:PL183–187, 1993.

Leu J.–G., et al. "Characterization of Polycolonal and Monoclonal Anti–Taxol Antibodies and Measurement of Taxol in Serum." *Cancer Research* 53:1388–1391, 1993.

Jaziri M., et al. "Enzyme–linked Immunosorbent Assay for the Detection and the Semi–quantitative Determination of Taxane Diterpenoids related to Taxol in *Taxus sp*. and Tissue Cultures." *J. Pharm. Belg.* 46(2):93–99, 1991.

Grothaus, P.G., et al. An enzyme immunoassay for the determination of taxol and taxanes in *Taxus sp*. tissues and human plasma.

Sevier, E.D., et al. "Monoclonal antibodies in Clinical Immunology." *Clinical Chemistry* 27(11):1797–1806, 1981.

Van Vunakis, H. Radioimmnoassays: An Overview. Methods in Enzymology 70:201–209, 1980.

Odell, W. Use of Charcoal to Separate Antibody Complexes FromFfree Ligand in radioimmunoassay. Methods in Enzymology 70:274–279, 1980.

Johnstone A., and Thorpe, R. Immunochemistry in Practice. Blackwell Scientific Publications, London, 1987, pp. 246–249.

Harlome, E. and Lane, D. Antibodies: A Laboratory Manual. Cold Spring Harbor Laboratory, New York, 1988, pp. 148–240, 321–358.

Erlanger, B.F. The Preparation of Antigenic Hapten–Carrier Conjugates: A Survey. Methods in Enzymology 70:85–104, 1980.

*Primary Examiner*—Paula K. Hutzell
*Assistant Examiner*—Heather A. Bakalyar
*Attorney, Agent, or Firm*—John P. White

[57] ABSTRACT

The present invention provides two monoclonal antibodies capable of binding to taxol and taxol-like substances which are produced by hybridomas designated 69E4A8E, having ATCC Accession No. HB11281 and 29B7B3C, having ATCC Accession No. HB11280. The present invention also provides a method for detecting the presence of taxol or a taxol-like substance in a sample, a method for screening for a ligand in a subject which is not being treated with taxol, an endogenous taxol-like substance in human serum detected by this screening method, a method of quantitatively determining the amount of taxol or taxol-like substance in a biological fluid sample and a kit for assaying for taxol or a taxol-like substance in a sample.

19 Claims, 3 Drawing Sheets

ENDOGENOUS TAXOL-LIKE SUBSTANCE IN HUMAN SERUM, MONOCLONAL ANTIBODIES DIRECTED THERETO AND METHODS OF ASSAYING THEREFOR

The invention described herein was made in the course of work under Grant No. 1 R 55 CA-55159 from the National Institutes of Health. The U.S. Government has certain rights in this invention.

BACKGROUND OF THE INVENTION

Throughout this application, various publications are referenced by Arabic numerals in parentheses. Full text citations of these publications can be found at the end of the specification, immediately preceding the claims. The disclosures of these publications in their entirety are hereby incorporated by reference into this application in order to more fully describe the state of the art as known to those skilled therein as of the date of the invention described and claimed herein.

Taxol, a compound extracted from the western yew, *Taxus brevifolia*, is a diterpenoid, which has a 20 carbon, skeleton, with a complex ester side chain at C-13 and an oxetane ring. Taxol was shown to have antitumor activity (1). Its underlying mechanism is to promote and stabilize microtubule assembly and inhibit disassembly to tubulin (2). The binding site of taxol in microtubules differs from that of other anti-tublin drugs, such as colchicine, podophyllotoxin and vinblastine, which inhibit tubulin polymerization (3, 4).

In clinical trials, taxol was found to be affective in the treatment of ovarian (5, 6) and breast cancer (7) and melanoma (8). As with all anti-cancer agents, there are side effects, in this case neutropenia, hypersensitivity reactions mucositis, neurological and possible cardiac toxicity were reported during clinical trials (9). It would be useful, therefore, to be able to measure taxol levels in patient under treatment in order to optimize treatment. A sensitive assay for measuring taxol levels is by HPLC (9, 10). In this application, we describe a polyclonal and two monoclonal antibodies that can be used to measure taxol levels in human serum with high sensitivity and is more amenable for the measurement of large numbers of samples. The monoclonal antibodies also have the potential to be used to screen for taxol or taxol-like substances in extracts of natural products.

The three dimensional structure of taxol has an inverted cup-like shape. Gueritte-Voegelein et al. (16, 18) determined the three dimensional structure of taxotere, a semi-synthetic biologically active taxol analogue, by X-ray analysis; it also has an inverted cup shape and the same skeleton as taxol. The taxotere molecule is stabilized by intramolecular hydrogen bonds between C-3'H and the C-4 acetyl group and between C-2'H and C-18H$_3$, as well as a repulsive interaction between the substituents at C-2', C-3' and the taxane skeleton (16).

Structure-activity studies have revealed that the C-13 ester side chain (19, 20) and a closed oxetane ring (10, 21) are crucial to the activity of taxol derivatives. Opening of the oxetane ring results in considerable conformational change of the molecule (10, 21). Modification of substituents at C-10 and/or C-17 can alter activity but not markedly (10, 19, 20).

This application describes three antibodies specific for taxol: one rabbit antiserum and two monoclonal antibodies. With respect to the monoclonal antibodies, one is an IgG (69E4A8E) and the other an IgM (29B7B3C). All of them bind taxol and active derivatives well and can be used to measure taxol levels in human serum.

SUMMARY OF THE INVENTION

The present invention provides a monoclonal antibody which is capable of binding to taxol and taxol-like substances and is produced by a hybridoma cell designated 69E4A8E, having ATCC Accession No. HB11281. The present invention also provides a second monoclonal antibody capable of binding to taxol or taxol-like substances produced by a hybridoma cell designated 29B7B3C and having ATCC Accession No. HB11280.

The present invention also provides a method for detecting the presence of taxol or a taxol-like substance in a sample which comprises treating the sample with either of the above-identified monoclonal antibodies permitting the taxol or taxol-like substance in the sample to bind to the monoclonal antibody, removing antibodies which did not bind to taxol or the taxol-like substance, and detecting the presence of any bound antibodies, thereby detecting the presence of taxol or the taxol-like substance in the sample.

The present invention also provides a method for detecting the presence of taxol or a taxol-like substance in a sample which comprises contacting a predetermined amount of taxol or taxol-like substance labeled with a detectable marker with either of the above-identified monoclonal antibodies under conditions permitting the monoclonal antibody to bind to the detectably labeled taxol or taxol-like substance, contacting the sample with the complex such that any taxol or taxol-like substance in the sample will displace the detectably labeled taxol or taxol-like substance bound to the monoclonal antibody, separating any bound, labeled or unlabeled taxol or taxol-like substance from unbound, labeled or unlabeled taxol or taxol-like substance, and detecting the presence of any bound, detectably labeled taxol or taxol-like substance, thereby detecting the presence of taxol or taxol-like substance in the sample.

The present invention further provides a method for screening for a ligand in a subject which is not being treated with taxol which comprises obtaining a sample from a subject, contacting the sample with either of the above-identified monoclonal antibodies permitting the taxol or taxol-like substance in the sample to bind to the monoclonal antibody, removing antibodies which did not bind to taxol or the taxol-like substance, and detecting the presence of any bound antibodies in the sample, thereby detecting the presence of taxol or the taxol-like substance in the subject.

The present invention also provides an endogenous taxol-like substance in human serum which can be detected by the above-identified method.

The present invention further provides a method of quantitatively determining the amount of taxol or taxol-like substance in a biological fluid sample which comprises contacting a solid support with an excess of a composition of matter comprising taxol and an appropriate carrier molecule, contacting a predetermined amount of a biological fluid sample and a predetermined amount of either of the above-identified monoclonal antibodies permitting the taxol or taxol-like substance in the sample to bind to the monoclonal antibody, contacting the solid support to which the composition of matter is attached with the solution permitting antibodies which do not form a complex with the taxol or taxol-like substance in the biological fluid sample to bind to the composition of matter, treating the solid support so that only the composition of matter and monoclonal antibody bound thereto remain, and determining the amount of antibody bound to the composition of matter, thereby determining the concentration of taxol or taxol-like substance in the biological fluid sample.

The present invention further provides a method of quantitatively determining the amount of taxol or taxol-like substance in a sample which comprises contacting a predetermined amount of detectably labeled taxol or taxol-like substance with either of the above-identified monoclonal antibodies under conditions permitting the monoclonal antibody to bind to the detectably labeled taxol or taxol-like substance,. contacting the sample with the complex under appropriate conditions such that any taxol or taxol-like substance in the sample will displace the detectably labeled taxol or taxol-like substance bound to the monoclonal antibody, separating any bound, labeled or unlabeled taxol or taxol-like substance from unbound, labeled or unlabeled taxol or taxol-like substance, and determining the amount of bound, detectably labeled taxol or taxol-like substance, thereby determining the amount of taxol or taxol-like substance in the sample.

The present invention provides a kit for assaying for taxol or a taxol-like substance in a sample comprising in separate compartments either of the above-identified monoclonal antibodies, a second monoclonal antibody which is labeled with a detectable marker and is capable of binding to the antibody which is capable of binding to taxol or a taxol-like substance, and a standardized solution of taxol.

Finally, the present invention provides a method for the detection of taxol or taxol-like substances present in biological fluids during treatment with taxol or taxol like substances using the above-identified kit.

DETAILED DESCRIPTION OF THE INVENTION

Figure 1:
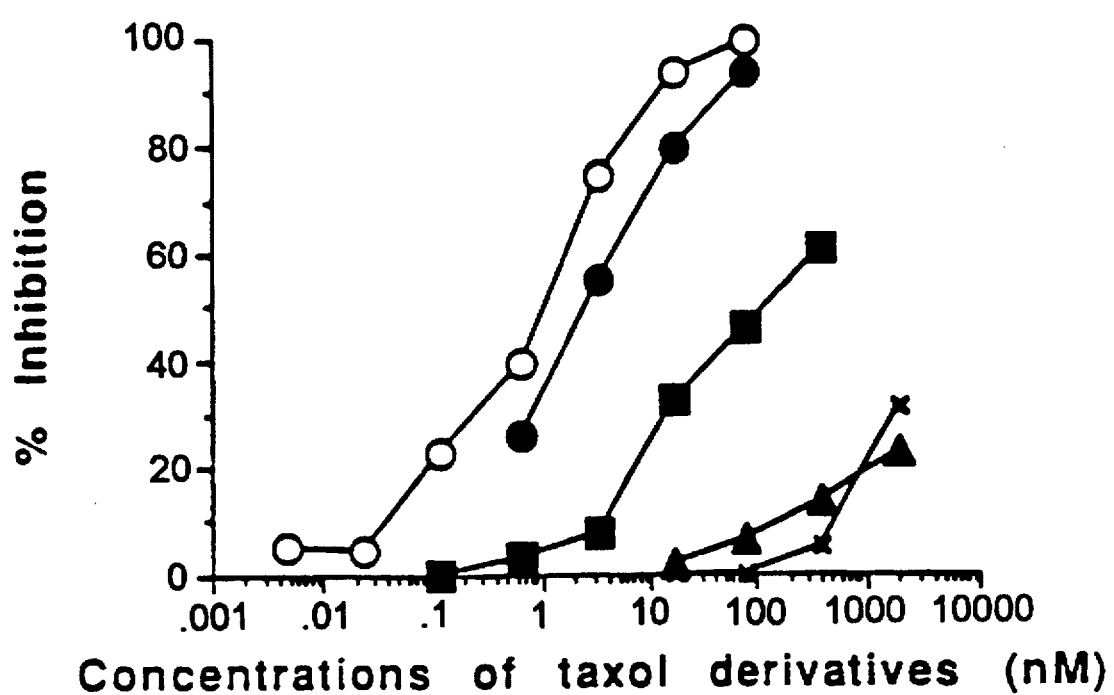
FIG. 1. Inhibition of the binding of rabbit anti-taxol antiserum to [$^3$H]taxol by taxol derivatives and analogues. ○, taxol; ◉, cephalomannine; ■, taxotere; ▲, baccatin III; X, 20-acetoxy-4-deacetyl-5-epi-20, O-secotaxol. The results are means of duplicate points and are expressed as the percentage in inhibition relative to the specific [$^3$H]taxol binding measured in the absence of inhibitors in RIA.

The present invention provides two monoclonal antibodies capable of binding to taxol or taxol-like substances. In one embodiment the monoclonal antibody is produced by a hybridoma cell designated 69E4A8E and having ATCC Accession No. HB11281. In a second embodiment the monoclonal antibody is produced by a hybridoma cell designated 29B7B3C and having ATCC Accession No. HB11280.

In one embodiment of the invention the monoclonal antibodies are capable of binding to taxol-like substances which are biologically active taxol derivatives. Those derivatives of taxol which are presently known to be biologically active are well known to those skilled in the art. At the time of this invention structure-activity studies have revealed that the C-13 ester side chain (19,20) and a closed oxetane ring (10,21) are crucial to the activity of taxol derivatives. In a preferred embodiment of this invention the monoclonal antibodies are capable of binding to biologically active taxol derivatives. It is anticipated that the monoclonal antibodies of the present invention will bind to any taxol-like substances presently known or later discovered, including later discovered biologically active taxol derivatives or taxol-like substances.

The present invention also provides hybridomas which produce the monoclonal antibodies capable of binding to taxol or taxol-like substances and are designated 69E4A8E (ATCC Accession No. HB11281) and 29B7B3C (ATCC Accession No. HB11280).

In one embodiment of this invention the monoclonal antibodies produced by the above-identified hybridomas are labeled with a detectable marker. Detectable markers useful for detecting monoclonal antibodies are well known to those skilled in the art and include, but are not limited to, radioactive isotopes, enzymes, dyes, fluorescent markers or biotin.

In one preferred embodiment the monoclonal antibodies are labeled with a radioactive isotope. In a second preferred embodiment the monoclonal antibodies are labeled with an enzyme.

The present invention also provides a method for detecting the presence of taxol or a taxol-like substance in a sample which comprises:

a) treating the sample with a monoclonal antibody capable of binding to taxol or taxol-like substances under conditions permitting the antibody to bind to taxol or the taxol-like substance and form a complex therewith;

b) removing antibodies which did not bind to taxol or the taxol-like substance; and c) detecting the presence of the antibodies, thereby detecting the presence of taxol or the taxol-like substance in the sample.

In one embodiment the monoclonal antibody is produced by a hybridoma cell designated 69E4A8E and having ATCC Accession No HB11281. In a second embodiment the monoclonal antibody is produced by a hybridoma cell designated 29B7B3C and having ATCC Accession No. HB11280.

The conditions permitting the binding of antibodies to taxol or taxol-like substances that may be present in a sample comprise incubation of a culture of monoclonal antibody and the sample. Incubation can be carried out at a temperature of from about 4° C. to about 37° C. for a period of from one half hour to 3 hours. In the preferred embodiment the incubation is carried at room temperature for 90 minutes.

The separation of unbound from bound monoclonal antibodies can be carried out by any method known to those skilled in the art. Examples include addition of charcoal to remove unbound taxol or taxol-like substance or by precipitation of the antibody-taxol complex with an anti-mouse globulin.

The detection of bound antibodies can be accomplished by known methods including, but not limited to, precipitation of the complex comprising antibody bound to taxol or taxol-like substance or by contacting the complex with an antibody capable of binding to the monoclonal antibody which is capable of binding to the taxol or taxol-like substance. Precipitation can be facilitated by known methods which include, but are not limited to addition of a ammonium sulfate solution, such as a 50% ammonium sulfate solution, or by addition of polyethylene glycol.

In one embodiment the detection step further comprises:
i) contacting the sample with a second antibody labeled with a detectable marker, wherein the second antibody is capable of binding to the antibody which is capable of binding to taxol or a taxol-like substance;
ii) removing any unbound antibody which is labeled with a detectable marker;
iii) detecting the presence of the detectable marker on an appropriate substrate, thereby detecting the presence of taxol or a taxol-like substance in the sample.

The labeled second antibodies which are capable of binding the monoclonal antibodies of the present invention can be produced by known methods. For example, the antibodies of the present invention are mouse IgG and IgM antibodies which can be detected by any anti-mouse IgG or IgM antibodies such as goat anti-mouse antibodies.

Detectable markers useful for the above method are well known to those skilled in the art and include, but are not limited to, radioactive isotopes, enzymes, dyes, fluorescent markers or biotin.

In one preferred embodiment the second monoclonal antibodies are labeled with a radioactive isotope. In another preferred embodiment the second monoclonal antibodies are labeled with an enzyme.

The sample which is being examined for the presence of taxol can be derived from an animal or plant. In one preferred embodiment of this invention the sample is plant extracts. In second preferred embodiment the sample is cytosols from cells which can be derived from animals or plants.

In a further embodiment the sample is a biological fluid taken from an animal. Biological fluids which are capable of being tested for the presence of absence of compounds in an animal are well known to those skilled in the art. Examples of such fluids include, but are not limited to, mucus, serum, saliva, urine, blood, feces and extracts of tissue.

In one preferred embodiment of this invention the biological fluid is serum and in a second preferred embodiment of this invention the biological fluid is urine.

In one embodiment of this invention when the sample is human serum the method further comprises a dilution step where the sample is diluted approximately 1:5 with a suitable diluent. Diluents suitable for this step will be readily apparent to those skilled in the art and include, but are not limited to such diluents as PBS-Tween 20, at a concentration range of 0.1% to 0.5%, or tris-buffers. In the preferred embodiment, the diluent is 0.1% PBS-Tween 20.

The present invention further provides a method of detecting the presence of taxol or taxol-like substance in a sample which comprises:
a) contacting a predetermined amount of taxol or taxol-like substance labeled with a detectable marker with a monoclonal antibody capable of binding to taxol or taxol-like substances under conditions permitting the monoclonal antibody to bind to the detectably labeled taxol or taxol-like substance;
b) contacting the sample with the complex of step (a) such that any taxol or taxol-like substance in the sample will displace the detectably labeled taxol or taxol-like substance bound to the monoclonal antibody;
c) separating any bound, labeled or unlabeled taxol or taxol-like substance from unbound, labeled or unlabeled taxol or taxol-like substance; and
d) detecting the presence of any bound, detectably labeled taxol or taxol-like substance, thereby detecting the presence of taxol or taxol-like substance in the sample.

In one embodiment the monoclonal antibody capable of binding to taxol or taxol-like substances is produced by a hybridoma cell designated 69E4A8E and having ATCC Accession No. HB11281. In a second embodiment the monoclonal antibody is produced by a hybridoma cell designated 29B7B3C and having ATCC Accession No. HB11280. Detectable markers useful for labeling tax or taxol-like substances in the above method are well known to those skilled in the art and include, but are not limited to, radioactive isotopes, enzymes, dyes, fluorescent markers or biotin.

In the preferred embodiment the taxol or taxol-like substance is labeled with a radioactive isotope.

The conditions permitting the binding of antibodies to the detectably labeled taxol or taxol-like substances that may be present in a sample comprise incubation of a culture of monoclonal antibody and the sample. Incubation can be carried out at temperature range of from about 4° C. to about 37° C. for a period of from about one half hour to 3 hours. In the preferred embodiment the incubation is carried at room temperature for 2 hours.

The bound labeled or unlabeled taxol or taxol-like substance can be separated from the unbound labeled or unlabeled taxol or taxol-like substance by any method known to those with skill in the art. Examples of such methods include addition of a charcoal solution and centrifugation, precipitation of the complex comprising monoclonal antibody and the labeled or unlabeled taxol or taxol-like substance bound thereto or by contacting the complex with an antibody capable of binding to the monoclonal antibody which is capable of binding to the taxol or taxol-like substance.

Precipitation can facilitated by known methods which include, but are not limited to addition of an ammonium sulfate solution, such as a 50% ammonium sulfate solution, or by addition of polyethylene glycol.

The sample which is being examined for the presence of taxol can be derived from an animal or plant. In one preferred embodiment of this invention the sample is plant extracts. In second preferred embodiment the sample is cytosols from cells which can be derived from animals or plants.

In a further embodiment the sample is a biological fluid taken from an animal. Biological fluids which are capable of being tested for the presence of absence of compounds in an animal are well known to those skilled in the art. Examples of such fluids include, but are not limited to, mucus, serum, saliva, urine, blood, feces and extracts of tissue.

In one preferred embodiment of this invention the biological fluid is serum and in a second preferred embodiment of this invention the biological fluid is urine.

In one embodiment of this invention when the sample is human serum the method further comprises a dilution step where the sample is diluted approximately 1:5 with a suitable diluent. Diluents suitable for this step will be readily apparent to those skilled in the art and include, but are not limited to such diluents as PBS-Tween 20, at a concentration range of from about 0.1% to about 0.5%, or tris-buffers. In the preferred embodiment, the diluent is 0.1% PBS-Tween 20.

The present invention also provides a method for screening for a ligand in a subject which is not being treated with taxol which comprises:
a) obtaining a sample from a subject;
b) contacting the sample with a monoclonal antibody capable of binding to taxol or taxol-like substances under conditions permitting the antibody to any taxol-like substance in the sample and form a complex therewith;

c) removing any antibodies which did not bind to the taxol-like substance; and d) detecting the presence of antibodies in the sample, thereby detecting the presence of the ligand in the subject.

This method is useful for more closely studying the biological processes associated with the action of taxol or biologically active taxol derivatives and can be useful for identifying endogenous taxol-like substances.

In one embodiment the monoclonal antibody capable of binding to taxol or taxol-like substances is produced by a hybridoma cell designated 69E4A8E and having ATCC Accession No. HB11281. In a second embodiment the monoclonal antibody is produced by a hybridoma cell designated 29B7B3C and having ATCC Accession No. HB11280. The conditions permitting the binding of antibodies to taxol or taxol-like substances that may be present in a sample comprise incubation of a culture of monoclonal antibody and the sample. Incubation can be carried out at temperature range of from about 4° C. to about 37° C. for a period of from about one half hour to 3 hours. In the preferred embodiment the incubation is carried at room temperature for 2 hours.

The separation of unbound from bound monoclonal antibodies can be carried out by any method known to those skilled in the art. Examples include addition of charcoal to remove unbound taxol or taxol-like substance or by precipitation of the antibody-taxol complex with an anti-mouse globulin.

The detection of bound antibodies can be accomplished by known methods including, but not limited to, precipitation of the complex comprising antibody bound to taxol or taxol-like substance or by contacting the complex with an antibody capable of binding to the monoclonal antibody which is capable of binding to the taxol or taxol-like substance. Precipitation can be facilitated by known methods which include, but are not limited to addition of an ammonium sulfate solution, such as a 50% ammonium sulfate solution, or by addition of polyethylene glycol.

In one embodiment the detection step further comprises:

i) contacting the sample with a second antibody labeled with a detectable marker, wherein the second antibody is capable of binding to the antibody which is capable of binding to taxol or a taxol-like substance:

ii) removing any unbound antibody which is labeled with a detectable marker;

iii) detecting the presence of the detectable marker on an appropriate substrate, thereby detecting the presence of taxol or a taxol-like substance in the sample.

The labeled second antibodies which are capable of binding the monoclonal antibodies of the present invention can be produced by known methods. For example, the antibodies of the present invention are mouse IgG and IgM antibodies which can be detected by any anti-mouse IgG or IgM antibodies such as goat anti-mouse antibodies.

Detectable markers useful for the above method are well known to those skilled in the art and include, but are not limited to, radioactive isotopes, enzymes, dyes, fluorescent markers or biotin.

In one preferred embodiment the second monoclonal antibodies are labeled with a radioactive isotope. In another preferred embodiment the second monoclonal antibodies are labeled with an enzyme.

In a preferred embodiment the sample is a biological fluid taken from an animal. Biological fluids which are capable of being tested for the presence of absence of compounds in an animal are well known to those skilled in the art. Examples of such fluids include, but are not limited to, mucus, serum, saliva, urine, blood, feces and extracts of tissue.

In a preferred embodiment of this invention the animal is human and biological fluid is serum or urine.

In another embodiment of this invention the sample is cytosols from cells derived from the subject or from cell culture.

In one embodiment of this invention when the sample is human serum the method further comprises a dilution step where the sample is diluted approximately 1:5 with a suitable diluent. Diluents suitable for this step will be readily apparent to those skilled in the art and include, but are not limited to such diluents as PBS-Tween 20, at a concentration range of from about 0.1% to about 0.5%, or tris-buffers. In the preferred embodiment, the diluent is 0.1% PBS-Tween 20.

The present invention also provides a ligand recognized by the above-identified method. For the purposes of this invention, the "ligand" is an endogenous taxol-like substance which is capable of being bound by the monoclonal antibodies of the present invention. In one embodiment the ligand is an endogenous taxol-like substance which is bound by the monoclonal antibody produced by a hybridoma cell designated 69E4A8E and having ATCC Accession No. HB11281. In a second embodiment the ligand is an endogenous taxol-like substance which is bound by the monoclonal antibody produced by a hybridoma cell designated 29B7B3C and having ATCC Accession No. HB11280.

In a preferred embodiment, the endogenous taxol-like substance detected by the monoclonal antibodies of this invention are polypeptides.

This invention further provides a method of quantitatively determining the amount of taxol or taxol-like substance in a sample which comprises:

a) contacting a solid support with an excess of a composition of matter comprising taxol and an appropriate carrier molecule under conditions permitting the composition of matter to attach to the surface of the solid support;

b) contacting the solid support to which the composition of matter is attached with a suitable blocking agent or buffer;

c) contacting a predetermined amount of a biological fluid sample and a predetermined amount of a monoclonal antibody capable of binding to taxol or taxol-like substances under such conditions permitting the taxol or taxol-like substance in the sample to bind to the monoclonal antibody and form a complex therewith in solution;

d) contacting the solid support to which the composition of matter is attached with the solution of step (c) under conditions permitting antibodies which do not form a complex with the taxol or taxol-like substance in the biological fluid sample to bind to the composition of matter;

e) treating the solid support so that only the composition of matter and monoclonal antibody bound thereto remain; and f) determining the amount of antibody bound to the composition of matter, thereby determining the concentration of taxol or taxol-like substance in the biological fluid sample.

In one embodiment the monoclonal antibody capable of binding to taxol or taxol-like substances is produced by a hybridoma cell designated 69E4A8E and having ATCC Accession No. HB11281. In a second embodiment the monoclonal antibody is produced by a hybridoma cell designated 29B7B3C and having ATCC Accession HB11280. Carrier molecules which are useful to bind taxol or taxol-like substances to the solid support are well known to those skilled in the art and include, but are not limited to, proteins such as bovine serum albumin, rabbit serum albumin, keyhole limpet hemocyanin, thyroglobulin, or ovalbumin. In the preferred embodiment of this invention the carrier molecule is rabbit serum albumin.

Coating of the solid substrate with the complex comprising taxol or taxol-like substance and the carrier molecule can be carried out at 0° C. to room temperature for a period of one hour to 24 hours. In the preferred embodiment the solid substrate is contacted with an excess of the complex at 4° C. and stored overnight, approximately 18 hours.

Suitable blocking agents and buffers are well known to those skilled in the art and include but are not limited to, PBS-Tween 20 or PBS containing fetal calf serum or bovine serum. In the preferred embodiment the blocking is conducted with PBS containing 1% fetal calf serum. Blocking is accomplished by incubating at temperature of approximately 37° C. for about 1 hour.

The conditions permitting the binding of antibodies to taxol or taxol-like substances that may be present in a sample comprise incubation of a culture of monoclonal antibody and the sample. Incubation can be carried out at room temperature for a period of one half to 3 hours. In the preferred embodiment the incubation is carried at room temperature for 90 minutes.

The separation of unbound from bound monoclonal antibodies can be carried out by any method known to those skilled in the art, including but not limited to washing several times with PBS. In the preferred embodiment, the separation is accomplished by washing three times with PBS-Tween 20.

The detection of bound antibodies can be accomplished by known methods including, but not limited to, contacting the complex with an antibody capable of binding to the monoclonal antibody which is capable of binding to the taxol or taxol-like substance. For example, the antibodies of the present invention are mouse IgG and IgM antibodies which can be detected by any anti-mouse IgG or IgM antibodies such as goat anti-mouse antibodies.

The sample which is being examined for the presence of taxol can be derived from an animal or plant. In one preferred embodiment of this invention the sample is plant extracts. In second preferred embodiment the sample is cytosols from cells which can be derived from animals or plants.

In a further embodiment the sample is a biological fluid taken from an animal. Biological fluids which are capable of being tested for the presence of absence of compounds in an animal are well known to those skilled in the art. Examples of such fluids include, but are not limited to, mucus, serum, saliva, urine, blood, feces and extracts of tissue.

In one preferred embodiment of this invention the biological fluid is serum and in a second preferred embodiment of this invention the biological fluid is urine.

This invention further provides a method of quantitatively determining the amount of taxol or taxol-like substance in a sample which comprises:

a) contacting a predetermined amount of detectably labeled taxol or taxol-like substance with a monoclonal antibody capable of binding to taxol or taxol-like substances under conditions permitting the monoclonal antibody to bind to the detectably labeled taxol or taxol-like substance;

b) contacting the sample with the complex of step (a) under appropriate conditions such that any taxol or taxol-like substance in the sample will displace the detectably labeled taxol or taxol-like substance bound to the monoclonal antibody;

c) separating any bound, labeled or unlabeled taxol or taxol-like substance from unbound, labeled or unlabeled taxol or taxol-like substance; and d) determining the amount of bound, detectably labeled taxol or taxol-like substance, thereby determining the amount of taxol or taxol-like substance in the sample.

In one embodiment the monoclonal antibody capable of binding to taxol or taxol-like substances is produced by a hybridoma cell designated 69E4A8E and having ATCC Accession No. HB11821. In a second embodiment the monoclonal antibody is produced by a hybridoma cell designated 29B7B3C and having ATCC Accession No. HB11280. Detectable markers useful for labeling taxol or taxol-like substances in the above method are well known to those skilled in the art and include, but are not limited to, radioactive isotopes, enzymes, dyes, fluorescent markers or biotin.

In the preferred embodiment the taxol or taxol-like substance is labeled with a radioactive isotope.

The conditions permitting the binding of antibodies to the detectably labeled taxol or taxol-like substances that may be present in a sample comprise incubation of a culture of monoclonal antibody and the sample. Incubation can be carried out at room temperature for a period of one half hour to 3. In the preferred embodiment the incubation is carried at room temperature for 2 hours.

The bound labeled or unlabeled taxol or taxol-like substance can be separated from the unbound labeled or unlabeled taxol or taxol-like substance by any method known to those with skill in the art. Examples of such methods include addition of a charcoal solution and centrifugation, precipitation of the complex comprising monoclonal antibody and the labeled or unlabeled taxol or taxol-like substance bound thereto or by contacting the complex with an antibody capable of binding to the monoclonal antibody which is capable of binding to the taxol or taxol-like substance.

Precipitation can facilitated by known methods which include, but are not limited to addition of a sodium sulfate solution, such as a 50% sodium sulfate solution, or by addition of polyethylene glycol.

The sample which is being examined for the presence of taxol can be derived from an animal or plant. In one preferred embodiment of this invention the sample is plant extracts. In second preferred embodiment the sample is cytosols from cells which can be derived from animals or plants.

In a further embodiment the sample is a biological fluid taken from an animal. Biological fluids which are capable of being tested for the presence of absence of compounds in an animal are well known to those skilled in the art. Examples of such fluids include, but are not limited to, mucus, serum, saliva, urine, blood, feces and extracts of tissue.

In one preferred embodiment of this invention the biological fluid is serum and in a second preferred embodiment of this invention the biological fluid is urine.

In one embodiment of this invention when the sample is human serum the method above further comprises a dilution step where the sample is diluted approximately 1:5 with a suitable diluent. Diluents suitable for this step will be readily apparent to those skilled in the art and include, but are not limited to such diluents as PBS and tris-buffers.

The present invention further provides a kit for assaying for taxol or a taxol-like substance in a sample comprising in separate compartments:
   a) the monoclonal antibody capable of binding to taxol or taxol-like substances;
   b) a second monoclonal antibody which is capable of binding to the antibody which is capable of binding to taxol or a taxol-like substance; and
   c) a standardized solution of taxol.

In one embodiment the monoclonal antibody capable of binding to taxol or taxol-like substances is produced by a hybridoma cell designated 69E4A8E and having ATCC Accession No. HB11281. In a second embodiment the monoclonal antibody is produced by a hybridoma cell designated 29B7B3C and having ATCC Accession No. HB11280. In a preferred embodiment, the kit further comprises a plate having a plurality of wells, each well coated with a layer of a complex comprising taxol and a suitable carrier molecule.

In another embodiment, the second monoclonal antibody is labeled with a detectable marker and the kit further comprises an appropriate substrate to detect the detectable marker.

Detectable markers useful for labeling taxol or taxol-like substances in the above method are well known to those skilled in the art and include, but are not limited to, radioactive isotopes, enzymes, dyes, fluorescent markers or biotin. Substrates useful for detecting various detectable markers are well known to those skilled in the art.

Finally, the present invention provides a method for monitoring the treatment of a disease in a subject being treated with taxol or a taxol-like substance which comprises using the above-identified kit to determine the amount of taxol or taxol-like substance in a sample taken from the subject.

Diseases for which the above-identified kit would be useful are all those diseases for which taxol or taxol-like substances are used in the treatment. Examples of such diseases include but are not limited to breast cancer or ovarian cancer or diseases characterized by the presence of a melanoma.

The invention is further illustrated in the Experimental Details section which follow. The Experimental Details section and Examples contained therein are set forth to aid in an understanding of the invention. This section is not intended to, and should not be interpreted to, limit in any way the invention set forth in the claims which follow thereafter.

EXPERIMENTAL

I. Materials and Methods

A. Reagents

Taxol (NSC-125973, cephalomannine (NSC-318735), baccatin III (NSC-330753) and [$^3$H]taxol (23 Ci/mmol) (NSC-125973) were obtained from the National Cancer Institute. The following taxol derivatives were a generous gift from Dr. D. G. I. Kingston (Virginia Polytechnic Institute and State University, Blacksburg, Va.): 2'-(triethylsilyl) taxol, 7-epitaxol, 2-debenzoylisotaxol,2-[N-benzyloxycarbamyl (Cbz)]-β-alanyl)-7-oxo-5,6-dehydro-5-0-secotaxol, 20-acetoxy-4-deacetyl-5-epi-20.0-secotaxol, 10-deacetylbaccatin III and 7-(triethylsilyl) baccatin III. We thank Dr. P. Potier of the Institut de Chimie des Substances Naturelles (CNRS), Gif-Sur-Yvette, France and Dr. J.-L. Fabre of Rhone-Poulenc Rorer (France) for the sample of taxotere.

Bovine serum albumin (BSA), rabbit serum albumin (RSA), charcoal, polyvinylpyrrolidone (PVP) and succinic anhydride were purchased from Sigma Chemical Corp. (St. Louis, Mo.). Isobutylchloroformate and n-tributylamine were from Eastman Kodak Corp. (Rochester, N.Y). Dextran T70 was purchased from Pharmacia LKB Biotechnology (Uppsala, Sweden). Fetal calf serum (FCS) was from Hyclone (Logan, Utah). Peroxidase-conjugated goat anti-mouse IgG+IgM was purchased from TAGO (Burlingame, Calif.). The isotyping kit was from Zymed (San Francisco, Calif.).

B. Synthesis of 2'-hemisuccinyltaxol

The method of Deutsch et al. (11) was used with some modifications. Taxol (20 mg) and succinic anhydride (36 mg) were dried for 4 hours at room temperature under vacuum over $P_2O_5$ and dissolved in 480 ul of dry pyridine. After standing at room temperature overnight, the pyridine was removed under vacuum and the residue washed one with 2 ml of distilled water. Acetone (1 ml) was added, and distilled water was added dropwise to the acetone solution until a few crystals (2-hemisuccinyltaxol) appeared. The mixture was kept at 4° C. for 3 hours and the crystals were recovered by filtration and dried under vacuum. The product was obtained in 70% yield.

C. Synthesis of 2'-hemisuccinyltaxol-protein conjugates

A modification of the procedures developed by Jaziri et al. (12) was used. 2'-hemisuccinyltaxol (10 mg) was dissolved in 1 ml DMSO and 300 ul acetonitrile, and 50 ul (35 mg, 0.19 mmoles) of n-tributylamine was added. The mixture was cooled to 4° C. in a ice bath, and 25 ul (25 mg, 0.18 mmoles) of isobutylchloroformate was added to the mixture which was kept in the ice bath for another 30 min.

The solution was added dropwise into a BSA or RSA solution (25 mg, [3.73 ×10$^{-4}$ mmoles] in 3 ml distilled $H_2O$, pH=9.5, at 4° C.). The pH was adjusted immediately to 7.5 with 1 N HCl and the mixture kept at 4° C. overnight and dialyzed against PBS at 4° C. overnight.

D. Rabbit antibodies

A female New Zealand White Rabbit was immunized intradermally along the back, with a 1:1 (v/v) mixture of 1 mg of 2'-hemisuccinyltaxol-BSA conjugate (taxol-BSA) in PBS and complete Freund's adjuvant (CFA). The rabbits were boosted with 0.5 mg of taxol-BSA incomplete Freud's adjuvant (IFA) at 3–4 week intervals and bled weekly following each boost.

E. Monoclonal antibodies (MAbs)

BALB/c mice (Charles River) were immunized i.p. with 0.5 mg taxol-BSA emulsified in CFA. Mice were boosted twice at two or three week intervals with 0.25 mg of taxol-BSA emulsified in IFA. Five days before the fusion, the mice were injected i.p. with 0.25 mg of taxol-BSA in PBS. Spleen cells were fused with nonsecreting myeloma cells P3 ×63-Ag8.653 (13), according to the method of Sharon et al. (14). Three weeks later, the hybridoma supernatant was assayed for the presence of anti-taxol antibodies by ELISA (see below). The positive clones were confirmed for taxol binding by a competitive ELISA (see below). Clones positive by competitive ELISA were subcloned twice by limiting dilution. Ascites were obtained by injecting 10$^6$ to 10$^7$ cells i.p. into BALB/c mice that had been primed with IFA i.p. 5 days before.

F. ELISA for anti-taxol MAb screening

Polystyrene microplates (Corning 25855) were coated with 100 ul of taxol-RSA (250ng/ml) in 0.1M sodium bicarbonate, PH=9.3, overnight at 4° C. The plates were washed with PBS containing 0.1% Tween 20 (PBS-T-20) three times, and 100 ul of culture supernatants were incubated in the wells for 2 hours at 37° C. The plates were washed three times with PBS-T-20 and 100 ul of a 1/3000 dilution of horseradish peroxidase-labeled goat anti-mouse IgG+IgM in PBS-Tween 20 was added to each well and incubated at 37° C. for 1 hour. After washing the plates three times with PBS-Tween 20, 100 ul of substrate (7 mg o-phenylenediamine dihydrochloride in 10 ml of 0.1M citrate-phosphate buffer, pH=5, containing 5 ul of 30% $H_2O_2$ was added to each well. The reaction was stopped after 10 min by the addition of 40 ul of 8N $H_2So_4$, and the absorbance of each well measured at 490 nm on a Dynatech Microplate reader.

G. Competitive ELISA

Polystyrene microplates were coated with 100 ul of taxol-RSA (250ng/ml) in 0.1 M sodium bicarbonate, pH=9.3, overnight at 4° C. The wells were washed with PBS-T-20 three times and blocked with 200 ul of PBS, containing 1% fetal calf serum, for 1 hour at 37° C. Culture supernatant (100 ul) was added to the coated plate either in the presence or in the absence of 50 uM taxol in PBS-T-20 (from a 10 mM taxol stock sodium in dimethyl sulfoxide), followed by incubation at room temperature for 90 min. After washing four times with PBS-T-20, bound antibodies were detected with 100 ul of 1/3000 dilution of peroxidase-labeled goat anti-mouse IgG+IgM in PBS-T-20 for 1 hour at 37° C. Color was developed and absorbance was measured as described above.

For those dose dependent inhibition of binding of anti-taxol to taxol-RSA, 100 ul of diluted MAb IgM (29B73C) or MAb IgG (69E4A8E) ascites was added to the coated well with serial dilutions of taxol or its derivatives, from 0.1 mM to 0.24 nM (all derivatives were from a $10^{-2}$M stock solution in DMSO), in PBS-T-20+2.5% FCS+3.5% polyvinyl pyrrolidone (PVP)+1% DMS).

II. Determination of taxol in human serum

A. ELISA

First a standard curve was determined by adding a mixture of 50 ul of 1/8000 dilution of 69E4A8E ascites in PBS-T-20 and 50 ul of serial 5-fold dilutions of taxol (from 0.1 mM to 0.24 nM) in PBS-T-20 into the taxol-BSA-coated wells.

To measure taxol levels in human serum, different amounts of taxol in DMSO were added to human serum; the final concentration of DMSO was, in all cases, 0.5%. A mixture of 50 ul of 1/8000 dilution of 69E4A8E ascites and 50 ul of a 1/5 dilution of serum in PBS-T-20 was added to taxol-RSA-coated plates, followed by incubation at room temperature for 90 min. Bound antibodies were detected as described above.

B. Radioimmunoassay

For a standard curve of anti-taxol antibody binding to [$^3$H]taxol, 100 ul of diluted 29B7B3C or 69E4A8E ascites or rabbit antiserum in RIA buffer (PBS+0.1% T-20+0.1% gelatin+0.1% $NaN_3$) was incubated for 2 hours at room temperature with 100 ul of [$^3$H]taxol (Ca. 10,000 cpm) in RIA buffer, in the presence of 100 ul of serially diluted taxol solutions in RIA buffer. Bound ligand was separated from free by the addition of 100 ul of a 2.5% dextran-coated charcoal solution in RIA buffer, incubation for 3 min at 4° C. and centrifugation in an Eppendorf centrifuge for 2 min. The supernatant, containing bound [$^3$H]taxol, was counted for radioactivity. For characterizing the antiserum, taxol derivatives were incubated at room temperature for 2 hours with the rabbit antiserum and [$^3$H]taxol. Bound [$^3$H]taxol was determined as described above.

To measure taxol levels in human serum by RIA, 100 ul of 1/150 dilution of rabbit anti-taxol antiserum or 1/150 dilution of 69E4A8E ascites were added to 100 ul of [$^3$H]taxol in RIA buffer and 100 ul of undiluted to 1/100 dilution of human serum samples originally containing concentrations of taxol from 0.005 uM to 5 uM. For the higher concentrations, the sera were diluted with RIA buffer to bring the concentrations within the working range of the RIA (0.03 nM to 10 nM). After incubating for 2 hours at room temperature, bound [$^3$H]taxol was determined as described above.

III. Results

A. Characterization of antibodies

Antibodies generated in rabbits using a taxol-BSA conjugate wee assayed for specificity by RIA (FIG. 1). The antibodies bound taxol and cephalomannine with almost equal affinity. Two inactive derivatives, baccatin III and 20, O-secotaxol, were bound with affinities about 3 orders of magnitude lower than taxol. Taxotere, a biologically active compound (15, 16), was bound with 100-fold lower affinity than taxol.

Figure 2:
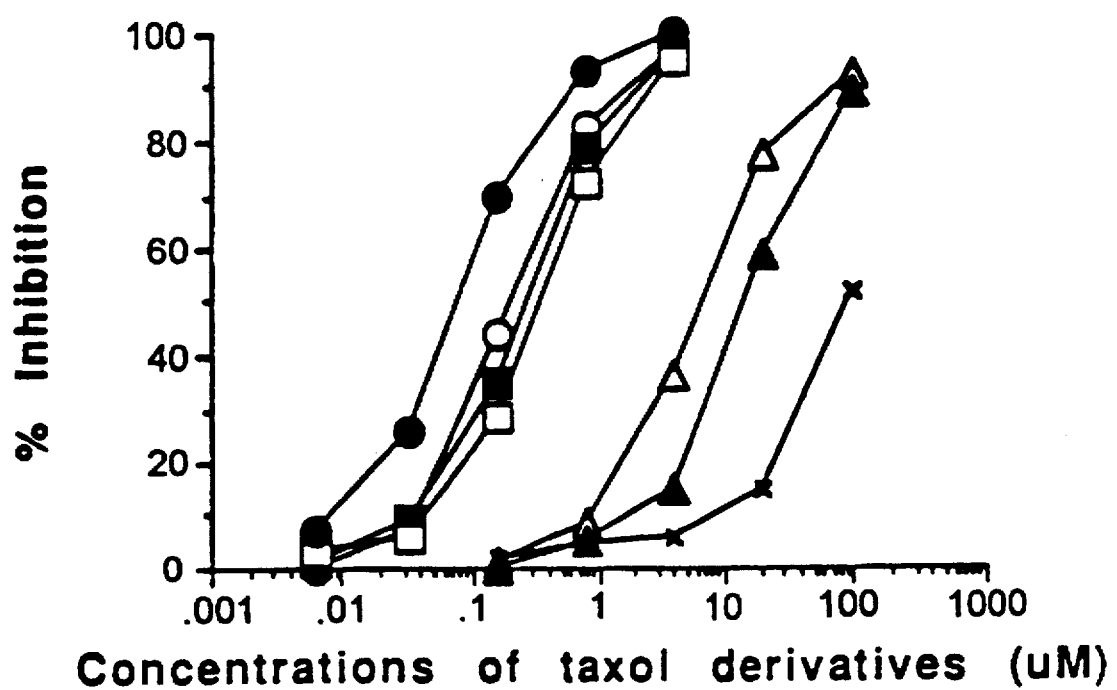
FIG. 2. Inhibition of the binding of 29B7B3C to taxol-RSA-coated wells by taxol derivatives and analogues. ○, taxol; ◉, cephalomannine; ■, taxotere; ▲, baccatin III; X, 20-acetoxy-4-deacetyl-5-epi-20, O-secotaxol □,7-epitaxol; and Δ, 2'- triethylsilyl) taxol. The results are means of duplicate points and are expressed as the percentage of inhibition relative to the absorbance at 490 nm measured in the absence of inhibitors in the ELISA.
Figure 3:
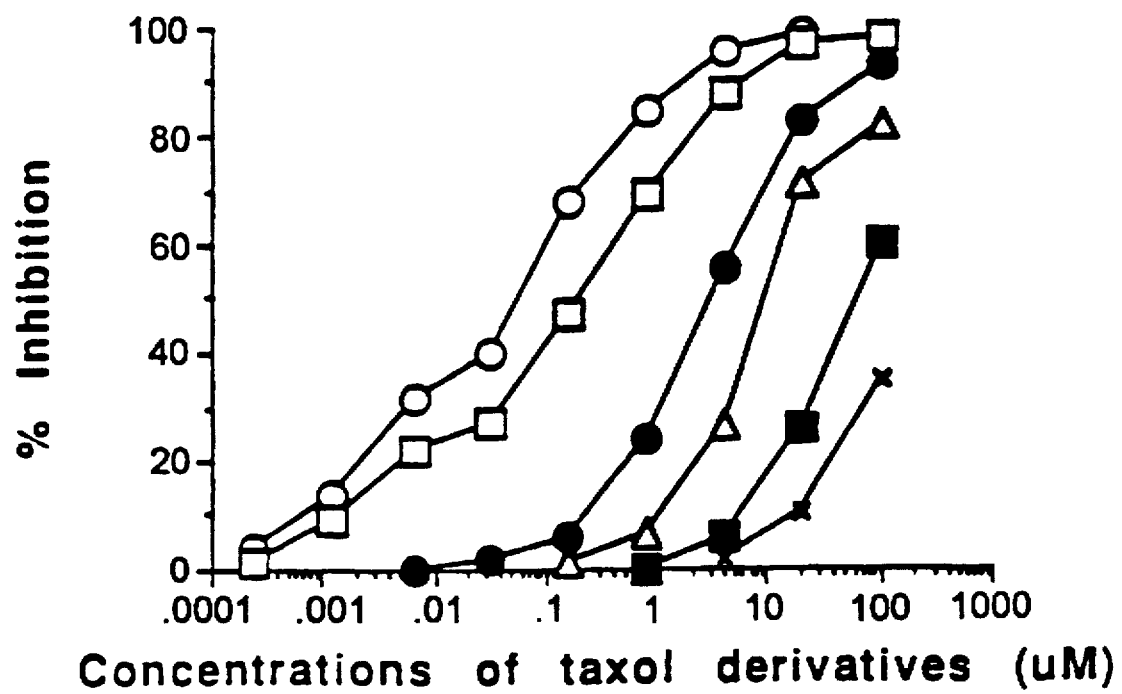
FIG. 3. Inhibition of the binding of 69E4A8E to taxol-RSA-coated wells by taxol derivatives and analogues. ○, taxol; ◉, cephalomannine; ■, taxotere; X, 20-acetoxy-4-deacetyl-5-epi-20, 0-secotaxol □,7-epitaxol; and Δ, 2'-triethylsilyl) taxol. The results are means of duplicate points and are expressed as the percentage of inhibition relative to the absorbance at 490 nm measured in the absence of inhibitors in the ELISA assay.

Two mouse monoclonal anti-taxol antibodies were isolated, 29B7B3C (IgM) and 69E4A8E ($IgG_1$). Taxol inhibited the binding of both antibodies to taxol-RSA, as shown by ELISA, with an $IC_{50}$ for taxol of about 0.1 uM. The specificities of the antibodies were determined by a competitive ELISA with taxol and 10 related derivatives. (FIGS. 2 and 3). Because many of the derivatives were not soluble in 5% DMSO at their high concentrations, PVP (3.5%) was introduced into the solution. Yonish-Rouach et al. (17) found that cyclosporin A, which is not soluble in water, could be solubilized in an aqueous solution containing 3.5% PVP (PVP (PH=7.4) without affecting immunological assays of cyclosporin A. We found that taxol and its derivatives were also more soluble in the presence of 3.5% PVP without any deleterious effect on the immunoassays (data not shown).

The $IC_{50}$ of each derivative, as determined by the ELISA inhibition assays (FIGS. 2 and 3), are shown in Table 1. Both monoclonal antibodies had higher binding affinities for biologically active derivatives (taxol, cephalomannine and 7-epitaxol) than for inactive derivatives (baccatin III derivatives and derivatives with an open oxetane ring). Specificity was consistent with the results of tubulin disassembly assays and cytotoxicity studies using the same taxol derivatives (10). An exception was the biologically active derivative taxotere which was recognized poorly by 69E4A8E. This had also been the case with the rabbit antiserum (see above).

B. Measurement of taxol levels in human serum by ELISA and RIA

For these experiments, known amounts of taxol were dissolved in human serum.

Taxol levels in human serum were measured by RIA using the rabbit antiserum. The results are in Table 2. The lowest concentration of taxol detected was 5 nM. However, the lower limit of measurement, as determined from the standard inhibition curve was 0.1 nM (0.085 ng/ml). The MAbs could also be used to measure taxol levels by RIA, but the lower limit of measurement was 50 nM (data not shown).

Taxol levels in human serum could be also measured by ELISA using 69E4A8E (Table 3). In preliminary experiments, we found that undiluted human serum partially blocked the binding of antibody to taxol-RSA as measured by ELISA. Interference of binding was minimized by a 1:5 dilution of the serum with PBS. The lower limit of measurements was about 50 nM or 42 ng/ml.

IV. Discussion

All of the antibodies are sensitive to the presence of the side chain ester at C-13 and an intact oxetane ring.

In other words, biologically active compounds are bound well and inactive derivatives are bound poorly. An exception is the inability of the rabbit serum and 69E4A8E to recognize taxotere, a semi-synthetic biologically active taxol analogue. The differences between taxol and taxotere lacks an C-19 acetyl group and has a t-butyloxycarbamido group rather than a benzamido group at the C-3' position. It is likely to be the latter that is the significant difference because the C-10 acetyl group is not necessary for activity. Moreover, cephalomannine, which is acetylated at C-10, is more poorly recognized by 69E4A8E. Apparently, the phenyl ring of taxol is an important determinant group for binding to the rabbit antibodies and to 69E4A8E.

On the other hand, 29B7B3C binds taxotere as well as it does taxol and it does not bind inactive derivatives well. We suggest, therefore, that it should be possible to use this antibody to screen for taxol or taxol-like compounds in extracts of natural products. We have begun to investigate this possibility. Moreover, its interaction with active taxol-related compounds closely correlates with their effects on microtubulin disassembly, making 29B7B3C an excellent candidate for eliciting anti-idiotypic antibodies that mimic taxol (22).

Our antibodies can measure taxol levels in human serum to which known quantities of taxol were added. In clinical trials, HPLC has been used to measure taxol levels in serum, urine and other biofluids, the lower limit of detection being 50 nM (9, 23). However HPLC techniques are not as suitable as immunoassays for routine analysis of large numbers of samples of biological fluids. The only immunoassay reported thus far is that of Jaziri et al. (12). Their rabbit antiserum could detect as little as 23.5 nM or 20 ng/ml in plant extracts by ELISA. They did not examine human serum. Our monoclonal antibodies could measure taxol in concentration range of about 10 nM to 1 um in PBS. However, the presence of human serum interfered with the binding of the antibodies in ELISA assays, requiring a dilution step that decreased the sensitivity of the procedure to a lower limit of 50 nM. The interfering factor in human serum did not seem to be an endogenous taxol-mimicking substance, because, upon dilution, its inhibition curve was not similar to that of taxol. Moreover, serum did not interfere with the RIAs. We will be investigating this further.

Rowinsky and Donehower (9) reviewed pharmacokinetic studies of taxol. In the doses recommended in phase II trials, i.e. 200 to 250 mg/m$^2$ infusion over 24 hours, the peak taxol level in plasma were above 0.6 uM, well within the range detectable and measured by our antibodies.

TABLE 1

Relative IC$_{50}$ of taxol derivatives in competitive ELISA, tubulin disassembly and cytotoxicity assays

| | Competitive ELISA | | Tubulin disassembly[a] | Cytotoxicity[a] (KBcells) |
|---|---|---|---|---|
| | 29B7B3C | 69E4A8E | | |
| Taxol | 1 | 1 | 1 | 1 |
| Cephalomannine | 0.4 | 44.2 | 1.5 | 3.2 |
| 7-Epitaxol | 1.7 | 3.1 | 3 | 3 |
| Taxotere | 1.2 | 1000 | 0.5 | 0.4[b] |
| 2'-(Triethylsiyl)taxol | 33.2 | 153.8 | — | 30,000[c] |
| 2'(N-cbz-B-alanyl)-7-oxo5,6-dehydro-5-O-secotaxol | >500 | >1000 | | |
| 20-Acetoxy-4-deacetyl-5-epi-20, O-secotaxol | 473.7 | >1000 | >21 | >100,000 |
| 2'-Debenzoyliso-taxol | | >500 | >1000 | — |

TABLE 1-continued

Relative IC$_{50}$ of taxol derivatives in competitive ELISA, tubulin disassembly and cytotoxicity assays

| | Competitive ELISA | | Tubulin disassembly[a] | Cytotoxicity[a] (KBcells) |
|---|---|---|---|---|
| | 29B7B3C | 69E4A8E | | |
| Baccatin III | 63.2 | >1000 | 52 | 1,700 |
| 10-deacetylbaccatin III | 63.2 | >1000 | 46 | 400 |
| 7-(Triethylsilyl)baccatin III | >500 | >1000 | 384[d] | — |

[a]All data are from reference 10.
[b]This value was from experiments using J774.2 cells; no data for KB cells is available.
[c]This value was from experiments using 2'-(t-butyldimethylsilyl)taxol, which is similar in structure to 2'-(triethysilyl)taxol.
[d]This value was from experiments using 7-acetylbaccatin III.

TABLE 2

Measurement of taxol levels in human serum by RIA using rabbit antitaxol antiserum.

| Actual taxol concentrations | Taxol concentrations found[a] |
|---|---|
| 5 uM | 5.87 ± 1.00 uM |
| 500 nM | 476 ± 4 nM |
| 50 nM | 32.7 ± 0.3 nM |
| 10 nM | 11.3 ± 0.5 nM |
| 5 nM | 5.67 ± 0.64 nM |

[a]All samples were done in duplicate.

TABLE 3

Measurement af taxol levels in human serum by ELISA using 69E4A8E.

| Actual taxol concentrations | Taxol concentrations found[a] |
|---|---|
| 5 uM | 3.61 ± 0.35 uM |
| 100 nM | 600 ± 144 nM |
| 50 nM | 62.1 ± 9.8 nM |

[a]Data were averaged from three duplicate experiments for each concentration.

REFERENCES

1. Wani, M. C., Taylor, H. L., Wall, M.E., Coggon, P., and McPhail, A. T. *J. Am. Chem. Soc.*, 93:2325–2327, 1971.
2. Schiff, P. B., Fant, J., and Horwitz, S. B. *Nature* (Lond.), 227:665–667, 1979.
3. Kumar, N. *J. Biol. Chem.*, 256:10435–10441, 1981.
4. Parnes, J., and Horwitz, S. B. *J. Cell. Biol.*, 91:479–487, 1981.
5. Thigpan, J. T., Blessing, J., and Bell, H. *Proc. Am. Soc. Clin. Oncol.*, 9:604, 1990.
6. Einzig, A. I., Wernik, P., and Sasloff, I. *Proc. Am. Assoc. Cancer Res.*, 31:1114, 1990.
7. Holmes, F. A., Frye, D., Theriault, R. L., Walters, R. S., Forman, A. D., Newton, L.K., Buzdar, A. U., and Hortobagyi, G. N. *Proc, Am. Soc. Clin. Oncol.*, 10:60, 1991.
8. Legha, S. S., Ring, S., Papadopoulos, N., Raber, M., and Benjamin, R. S. *Cancer* (Phila.), 65:2478–2481, 1990.
9. Rowinksy, E. K. and Donehower, R. C. *Pharmac. Ther.*, 52:35–84, 1991.
10. Kingston, D. G. I. *Pharmac. Ther.*, 52:1–34, 1991.
11. Deutsch, H. M., Glinski, J. A., Hernandez, M., Haugwitz, R. D., Narayanan, V. L., Suffness, M. and Zalkow, L. H. *J. Med. Chem.*, 32:788–792, 1989.

12. Jaziri, M., Diallo, B. M., Vanhaelen, M. H., Vanhaelen-Fastre, R. J., Zhiri, A., Becu, A. G. and Homes, J. *J. Pharm. Belg.*, 46:93–99, 1991.
13. Kearney, J. F., Radburch, A., Liesegang, B. and Rajewsky, K. *J. Immunol.*, 123:1548–1550, 1979.
14. Sharon, J., Morrison, S. L. and Kabat, E. A. *Proc. natl. Acad. Sci. U.S.A.*, 76:1420–1424, 1979.
15. Ringel, I. and Horwitz, S. B. *J. Natl. Cancer Inst.*, 83:288–291, 1991.
16. Gueritte-Voegelein, F., Guenard, D., Lavelle, F., Le Goff, M. -T., Mangatal, L. and Potier, P. *J. Med. Chem.*, 34:922–998, 1991.
17. Yonish-Rouach, E., Shinitzky, M. and Rubinstein, M. *J. Immunol. Meth.*, 135:147–153, 1990.
18. Gueritte-Voegelein, F., Guenard, D., Mangatal, L., Potier, P., Guilhem, J., Cesario, M. and Pascard, C. *Acta Crystalloqr.*, C46:781–784, 1990.
19. Parness, J., Kingston, D. G. I., Powell, R. G., Harracksigh, C. and Horwitz, S. B. *Biochem. biophys. Res. Commun.*, 105:1082–1089, 1982.
20. Lataste, H., Senilh, V., Wright, M., Guenard, D. and Potier, P. *Proc. Natl. Acad. Sci. U.S.A.*, 81:4090–4094, 1984.
21. Samaranayake, G., Magri, N. F., Jitrangsri, C. and Kingston, D. G. I. *J. Org. Chem.*, 56:5114–5119, 1991.
22. Erlanger, B. F. *Biochem. Soc. Transactions*, 19:138–143, 1991.
23. Longnecker, S. M., Donehower, R. C., Cates, A. E., Chen, T -L, Brundrett, R. B., Grochow, L. B., Ettinger, D. S. and Colvin, M. *Cancer Treat. Rep.*, 71:53–59, 1987.

What is claimed is:

1. A monoclonal antibody which specifically binds to taxol or biologically active taxol derivatives and which is produced by a hybridoma cell designated 69E4A8E and having ATCC Accession No. HB11281.

2. A monoclonal antibody which specifically binds to taxol or biologically active taxol derivatives and which is produced by a hybridoma cell designated 29B7B3C and having ATCC Accession No. HB11280.

3. The hybridoma cell designated 69E4A8E and having ATCC Accession. No. HB11281 which produces the monoclonal antibody of claim 1.

4. The hybridoma cell designated 29B7B3C and having ATCC Accession No. HB11280 which produces the monoclonal antibody of claim 2.

5. The monoclonal antibody of claims 1 or 2 labeled with a detectable marker.

6. The monoclonal antibody of claim 5, wherein the detectable marker is a radioactive isotope, enzyme, dye, fluorescent marker or biotin.

7. The monoclonal antibody of claim 5, wherein the detectable marker is a radioactive isotope.

8. The monoclonal antibody of claim 5, wherein the detectable marker is an enzyme.

9. A method of quantitatively determining the amount of taxol or biologically active taxol derivatives in a sample which comprises:

a) contacting a predetermined amount of detectably labeled taxol or biologically active taxol derivative with either of the monoclonal antibody of claims 1 or 2 under conditions permitting the monoclonal antibody to bind to the detectably labeled taxol or biologically active taxol derivative and form a complex therewith;

b) contacting the sample with the complex of step (a) under appropriate conditions such that any taxol or biologically active taxol derivative in the sample will displace the detectably labeled taxol or biologically active taxol derivative bound to the monoclonal antibody;

c) separating any bound, labeled or unlabeled taxol or biologically active taxol derivative from unbound, labeled or unlabeled taxol or biologically active taxol derivative; and d) determining the amount of bound, detectably labeled taxol or biologically active taxol derivative, thereby determining the amount of taxol or biologically active taxol derivative in the sample.

10. The method of claim 9, wherein in step (c), the bound labeled or unlabeled taxol or biologically active taxol derivative is separated from the unbound labeled or unlabeled taxol or biologically active taxol derivative by addition of a charcoal solution and centrifugation.

11. The method of claim 9, wherein in step (c), the bound labeled or unlabeled taxol or biologically active taxol derivative is separated from the unbound labeled or unlabeled taxol or biologically active taxol derivative by precipitation of the complex comprising monoclonal antibody and the labeled or unlabeled taxol or biologically active taxol derivative bound thereto.

12. The method of claim 11, wherein the precipitation is facilitated by addition of a sodium sulfate solution.

13. The method of claim 11, wherein the precipitation is facilitated by addition of polyethylene glycol.

14. The method of claim 9, wherein in step (c), the bound labeled or unlabeled taxol or biologically active taxol derivative is separated from the unbound labeled or unlabeled taxol or biologically active taxol derivative by contacting the complex formed in step (b) with an antibody which specifically binds to the monoclonal antibody which specifically binds to the taxol or biologically active taxol derivative.

15. The method of claim 9, wherein the sample is plant extracts.

16. The method of claim 9, wherein the sample is a biological fluid.

17. The method of claim 16, wherein the biological fluid is serum.

18. The method of claim 16, wherein the biological fluid is urine.

19. The method of claim 9, wherein the sample is cytosols from cells derived from animals or plants.

* * * * *

UNITED STATES PATENT AND TRADEMARK OFFICE
CERTIFICATE OF CORRECTION

PATENT NO. : 5,756,301
DATED : May 26, 1998
INVENTOR(S) : Bernard F. Erlanger, Jyh-Gang Leu, Bi-Xing Chen It is certified that error appears in the above-identified patent and that said Letters Patent is hereby corrected as shown below:

On the title page, item [54], "ENDOGENOUS TAXOL-LIKE SUBSTANCE IN HUMAN SERUM, MONOCLONAL ANTIBODIES DIRECTED THERETO AND METHODS OF ASSAYING THEREFOR" should read --AN ENDOGENOUS TAXOL-LIKE SUBSTANCE IN HUMAN SERUM, MONOCLONAL ANTIBODIES DIRECTED THERETO AND METHODS OF ASSAYING THEREFOR--

UNITED STATES PATENT AND TRADEMARK OFFICE
CERTIFICATE OF CORRECTION

PATENT NO. : 5,756,301
DATED : May 26, 1998
INVENTOR(S) : Bernard F. Erlanger, Jyh-Gang Leu, Bi-Xing Chen It is certified that error appears in the above-identified patent and that said Letters Patent is hereby corrected as shown below:

Column 1, line 1, "ENDOGENOUS TAXOL-LIKE SUBSTANCE IN HUMAN SERUM, MONOCLONAL ANTIBODIES DIRECTED THERETO AND METHODS OF ASSAYING THEREFOR" should read --AN ENDOGENOUS TAXOL-LIKE SUBSTANCE IN HUMAN SERUM, MONOCLONAL ANTIBODIES DIRECTED THERETO AND METHODS OF ASSAYING THEREFOR--.

Column 3, lines 42 and 50, "∆, 2'-triethylsilyl) taxol" should read --∆, 2'-(triethylsilyl) taxol--.

Column 10, line 19, "Accession No. HB11821" should read --Accession No. HB11281 --.

Column 12, line 43 "Freud's" should read --Freund's--.

Column 14, line 12 "wee" should read --were--.

Column 16, line 41 "100nM" should read --500nM"--.

Signed and Sealed this

Eighteenth Day of May, 1999

Attest:

Q. TODD DICKINSON

*Attesting Officer*       *Acting Commissioner of Patents and Trademarks*